United States Patent
Granqvist et al.

(10) Patent No.: US 10,469,241 B2
(45) Date of Patent: Nov. 5, 2019

(54) CLOCK SYNCHRONIZATION WITHIN WIRELESS NETWORK

(71) Applicant: Polar Electro Oy, Kempele (FI)

(72) Inventors: Niclas Granqvist, Mägenwil (CH); Patrick Celka, Neuchâtel (CH)

(73) Assignee: Polar Electro Oy, Kempele (FI)

( * ) Notice: Subject to any disclaimer, the term of this patent is extended or adjusted under 35 U.S.C. 154(b) by 0 days.

(21) Appl. No.: 15/474,387

(22) Filed: Mar. 30, 2017

(65) Prior Publication Data

US 2017/0359162 A1  Dec. 14, 2017

(30) Foreign Application Priority Data

Jun. 10, 2016  (GB) .................................. 1610175.0

(51) Int. Cl.
  *H04L 7/00* (2006.01)
  *H04W 4/70* (2018.01)
  (Continued)

(52) U.S. Cl.
  CPC ........ *H04L 7/0008* (2013.01); *A61B 5/02416* (2013.01); *A61B 5/0402* (2013.01); *A61B 5/1102* (2013.01); *H04W 4/70* (2018.02); *H04W 4/80* (2018.02); *H04W 56/0015* (2013.01); *H04W 84/18* (2013.01)

(58) Field of Classification Search
  CPC .............................. H04L 7/0008; H04W 4/005
  See application file for complete search history.

(56) References Cited

U.S. PATENT DOCUMENTS

| | | | | |
|---|---|---|---|---|
| 2007/0201591 A1* | 8/2007 | Knerr | ..................... | H04B 7/269 375/365 |
| 2014/0293851 A1* | 10/2014 | Abraham | .......... | H04W 52/0225 370/311 |

(Continued)

FOREIGN PATENT DOCUMENTS

| | | |
|---|---|---|
| CN | 102421187 A | 4/2012 |
| CN | 103338507 A | 10/2013 |

(Continued)

OTHER PUBLICATIONS

Combined Search and Examination Report, Application No. GB1610175.0, 8 pages, dated Jul. 18, 2016.

(Continued)

*Primary Examiner* — Jaison Joseph
(74) *Attorney, Agent, or Firm* — FisherBroyles, LLP

(57) ABSTRACT

A method of performing clock synchronization between two apparatuses includes storing, in a first apparatus, information representing synchronization accuracy required by at least one function of the apparatus; carrying out, by the first apparatus, a service discovery procedure with a second apparatus, and receiving clock information from the second apparatus during the service discovery procedure; determining, by the first apparatus on the basis of the received clock information and said stored information, whether or not synchronization accuracy is sufficient for the at least one function; and upon determining that the synchronization accuracy is sufficient for the at least one function, synchronizing a clock of the first apparatus with a clock of the second apparatus.

23 Claims, 4 Drawing Sheets

(51) Int. Cl.
*H04W 4/80* (2018.01)
*A61B 5/024* (2006.01)
*A61B 5/0402* (2006.01)
*A61B 5/11* (2006.01)
*H04W 56/00* (2009.01)
*H04W 84/18* (2009.01)

(56) References Cited

U.S. PATENT DOCUMENTS

| | | | | |
|---|---|---|---|---|
| 2015/0242608 A1* | 8/2015 | Kim | ............... | G06F 1/3231 |
| | | | | 726/19 |
| 2017/0010677 A1* | 1/2017 | Roh | ............... | G06F 3/0488 |
| 2017/0169695 A1* | 6/2017 | Poisner | ............. | A63F 13/46 |
| 2017/0196457 A1* | 7/2017 | Thakur | ............ | A61B 5/0031 |

FOREIGN PATENT DOCUMENTS

| | | | |
|---|---|---|---|
| CN | 105052181 A | 11/2015 |
| CN | 105515708 A | 4/2016 |
| WO | 2007100967 A2 | 9/2007 |

OTHER PUBLICATIONS

Response made to Report under Section 18(3), Application No. GB1610175.0, 1 page, Feb. 20, 2017.
Search Report/Office Action issued by the State Intellectual Property Office of the People's Republic of China in relation to corresponding Chinese patent application No. 201710412892.X dated Nov. 27, 2018, 10 pgs.

* cited by examiner

CLOCK SYNCHRONIZATION WITHIN WIRELESS NETWORK

CROSS-REFERENCE TO RELATED APPLICATION

This application claims benefit to Great Britain Application No. 1610175.0, filed Jun. 10, 2016, which is incorporated by reference herein in its entirety.

BACKGROUND

Field

The present invention relates to synchronization of clocks within a wireless network such as a personal area network (PAN).

Description of the Related Art

Internet of things concept is being developed all the time. In relation to such applications, stationary and wearable devices may be provided with networking capabilities. As the technology advances, cooperation between the wearable devices is also being developed. Some applications may require accurate clock synchronization between the wearable devices.

SUMMARY

The present invention is defined by the subject-matter of the independent claims. Embodiments are defined in the dependent claims.

BRIEF DESCRIPTION OF THE DRAWINGS

In the following the invention will be described in greater detail by means of preferred embodiments with reference to the accompanying drawings, in which.

DETAILED DESCRIPTION

The following embodiments are exemplifying. Although the specification may refer to "an", "one", or "some" embodiment(s) in several locations of the text, this does not necessarily mean that each reference is made to the same embodiment(s), or that a particular feature only applies to a single embodiment. Single features of different embodiments may also be combined to provide other embodiments.

Figure 1:
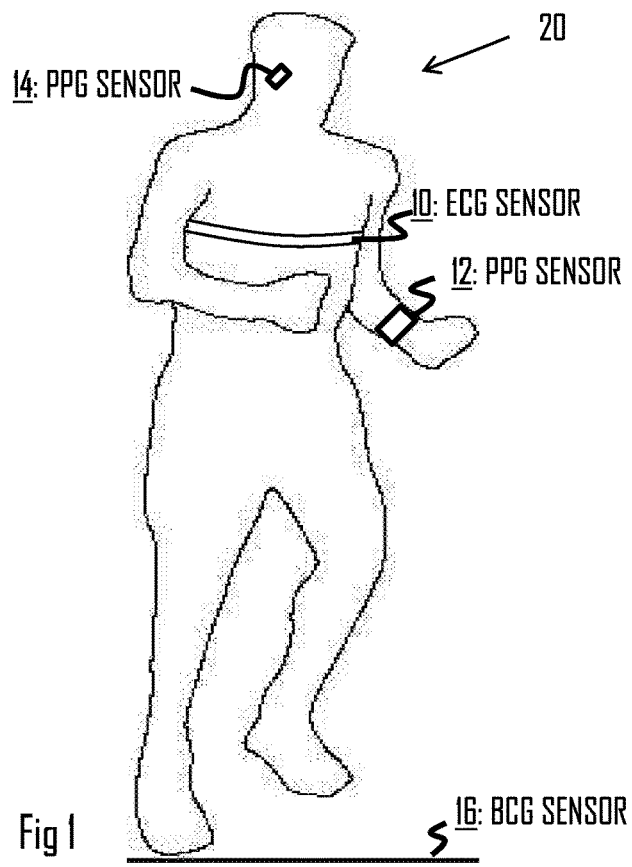
FIG. 1 illustrates a measurement system to which embodiments of the invention may be applied.

FIG. 1 illustrates a measurement system comprising sensor devices that may be used in the context of some embodiments of the present invention. At least some of the sensors may be wearable sensor devices. The sensors may employ one or more measurement technologies for measuring heart activity of a user 20. For example, at least one sensor device 10 may be configured to measure electrocardiogram (ECG) of the user 20. Such an ECG sensor 10 may comprise one or more electrodes arranged to be in contact with the user's 20 skin in order to measure electric charges generated during each heartbeat. The ECG sensor may be portable to enable the measurement during an outdoors physical exercise, such as running or cycling.

At least one sensor device 12, 14 may be configured to measure a photoplethysmogram (PPG) optically. PPG represents a volumetric measurement of an organ. A PPG sensor 12, 14 may comprise a light source such as a light emitting diode (LED) configured to illuminate a skin of the user 20 and, further, comprise a light-sensitive sensor such as a photodiode configured to measure changes in light reflected from the illuminated skin. With each cardiac cycle, the heart pumps blood to peripherial arteries. Even though this blood wave pulse is damped by the artery system as it propagates, it is enough to distend arteries and arterioles in the subcutaneous tissue. If the light source and the light-sensitive sensor are place appropriately against the skin, the blood wave pulse can be detected as a change in the reflecting light measured by using the light-sensitive sensor. Each cardiac cycle appears as a peak in a measurement signal acquired through the light-sensitive sensor. The blood pulse wave may be modulated by multiple other physiological systems and, therefore, the PPG may also be used to monitor breathing, hypovolemia, and other physiological conditions. The PPG may be measured at various locations of the human body, e.g. from a wrist (sensor 12), head, ear canal or ear leaf (sensor 14).

At least one sensor device 16 may be configured to measure a ballistocardiogram (BCG). The BCG is a measure of ballistic forces generated during the heartbeat. Ballistocardiogram characterizes motion of the human body resulting from the ejection of blood into the great vessels during each heartbeat. The BCG shows on a frequency range between 1 and 20 Hertz (Hz), and is caused by the mechanical movement of the heart. As the ECG and the PPG, the BCG can be recorded by using a non-invasive sensor 16 from the surface of the body. The BCG sensor 16 may be a ballistocardiographic scale configured to measure a recoil of the human body standing on the scale. The recoil is caused by the heartbeat and can be measured from the user standing on the BCG scale, e.g. by using a pressure sensor. The BCG scale may be configured to show the user's 20 heart rate as well as weight.

The above-described sensor devices may be used to carry out measurements of physiological characteristics of the user 20, such as cardiovascular characteristics. One example of using distributed cardiovascular measurements is measurements of a blood pulse travelling through the user's body. The blood pulse is modulated on its way through the human body. The modulation may be caused by various physiological conditions and functions. Therefore, characteristics of the blood pulse wave may comprise representation of such physiological conditions. One set of such characteristics may include propagation characteristics of the blood pulse wave. The propagation characteristics may be considered as time characteristics that represent a pulse transit time (PTT), for example, within a certain distance in the human arteries. Equivalent characteristics may include pulse propagation velocity which is proportional to the pulse transit time and, therefore, can be considered to represent the time characteristics of the blood pulse wave.

The time characteristics of the blood pulse wave may be measured by using at least two measurements associated with different locations of the human body. The at least two measurements may be carried out by different sensor devices that communicate with one another over a wireless link. Since the different sensor devices measure the same blood pulse wave, the measurements may be synchronized with each other. When the measurements are carried out by sensors comprised in the same device or the same casing, the measurements may be synchronized by synchronizing the measurements to the same clock signal provided by a clock signal generator of the device. When the measurements are carried out by physically separated sensor devices, e.g. the ECG sensor 10 and the PPG sensor 12, the two devices may be synchronized to a common clock through other means. The synchronization accuracy may depend on precision accuracy required of the computed metric. In embodiments where the sensor devices are provided in different, physically separate devices, the devices may be synchronized to a common clock such as a clock of Global Positioning System or another satellite navigation system providing an accurate clock signal for both devices. Some wireless communication protocols provide synchronization tools, and some embodiments may use such tools to carry out the synchronization. Some embodiments are described below.

Figure 2:
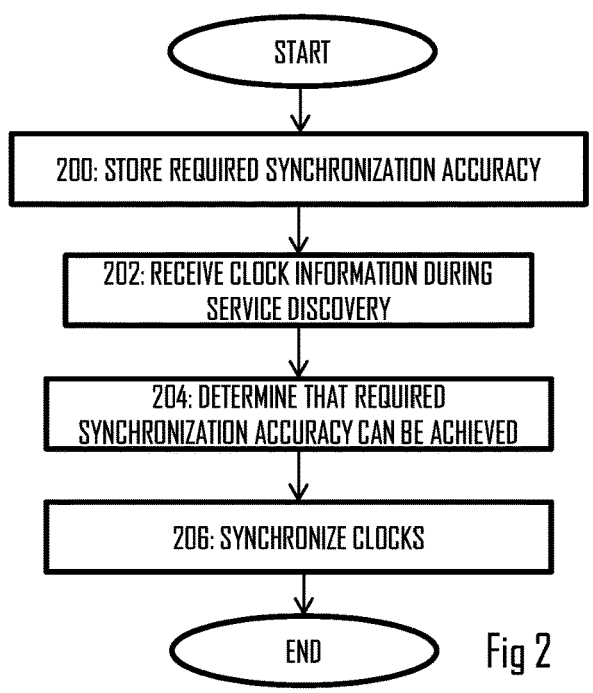
FIG. 2 illustrates a process for evaluating clock synchronization according to an embodiment of the invention.

Different systems may enable different degrees of synchronization accuracy. The achievable synchronization accuracy may depend on the system configuration, characteristics of individual devices or their components, such as a clock signal generator, crystals, connection quality, etc. In general, there are various aspects that may affect the synchronization accuracy. Even though a system may be configured such that a certain degree of synchronization accuracy is achievable, in real life situations the degree of synchronization accuracy may be variable and fall below accuracy required by a certain application. FIG. 2 illustrates a flow diagram of a process for carrying out a check for the achievable synchronization accuracy before proceeding with the synchronization. The process may be carried out in an apparatus that may be any one of the above-described sensor devices 10 to 16 or another apparatus. Referring to FIG. 2, the process comprises in the apparatus: storing information representing synchronization accuracy required by at least one function of the apparatus (block 200); carrying out a service discovery procedure with a second apparatus and receiving clock information from the second apparatus during the service discovery procedure (block 202); determining, on the basis of the received clock information and said stored information, whether or not synchronization accuracy is sufficient for the at least one function (block 204) and, upon determining that the synchronization accuracy is sufficient for the at least one function, synchronizing a clock of the first apparatus with a clock of the second apparatus.

Determining the required versus achievable synchronization accuracy beforehand provides the apparatus with capability of evaluating whether or not it can operate the function requiring the synchronization.

In an embodiment, the clock information received from the second apparatus comprises clock accuracy of the second apparatus. The clock accuracy may indicate drifting of a clock of the second apparatus, for example. The clock accuracy may be indicated in a discovery message transmitted by the second apparatus during the service discovery. The service discovery may be carried out according to specifications of Bluetooth protocol or another IEEE 802.15-based protocol or another wireless protocol. The wireless protocol may be designed for personal area networking (PAN). In the embodiment of Bluetooth, the service discovery may comprise advertisement service discovery and/or a generic attribute profile (GATT) service discovery according to an attribute protocol of the Bluetooth. In the advertisement service discovery, a server device providing a Bluetooth service may advertise the service by transmitting a universally unique identifier (UUID) of the service and information describing the service. The service may be a measurement service, for example, or another type of service. In the context of the embodiments described herein, the service may be associated with the requirement of synchronizing devices using the service. The advertisement may be carried out by transmitting or broadcasting an advertisement message on an advertisement channel. A client device may scan the advertisement channel(s) and detect the availability of the service. If the client device is configured, by an application layer for example, to use the service, the client device may transmit a connection request to the server device. Thereafter, a connection may be setup between the server device and the client device. After the connection setup, the client device may request for detailed characteristics and parameters of the service from the server device through the GATT service discovery. During the GATT service discovery, the client device acquires further information on the service and parameters and data structures related to service. The server device and the client device may negotiate the master and slave roles during the connection setup.

Figure 3:
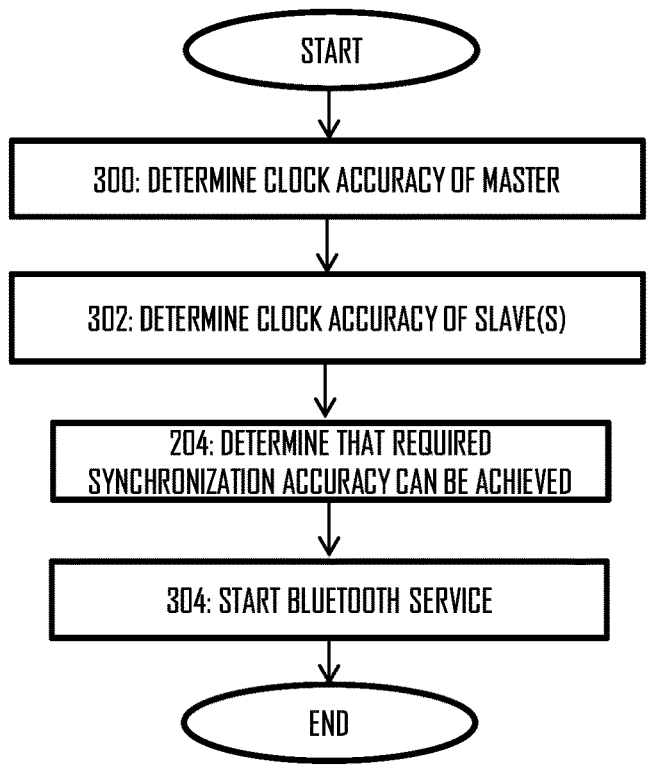
FIG. 3 illustrates an embodiment of a process for initiating a service on a basis of clock information exchange during a service discovery procedure.

FIG. 3 illustrates a process for using the clock accuracy in connection with Bluetooth.

Referring to FIG. 3, the process may be carried out in the above-described apparatus. The apparatus may be configured to operate as a master device or a slave device of a Bluetooth network. The apparatus may be a client device scanning for a Bluetooth service provided by a server device. The service may be a measurement service such as a heart activity measurement service, or it may be a control service, or another type of a service. The scanning may be triggered by an application executed in the apparatus. In block 300, the apparatus determines the clock accuracy of the master device. If the apparatus is the master device, it may determine accuracy of its own clock. For example, the clock drifting is a parameter available to the device. If the apparatus is the slave device, it may receive the clock accuracy from the master device during the advertisement, during the service discovery and/or after the service discovery and completion of associated connection setup. For example, sleep clock accuracy (SCA) is a parameter defined in Bluetooth specifications, and it can be used as an indicator of the clock accuracy. In block 302, the apparatus determines the clock accuracy of one or more slave devices. If the apparatus is the slave device, it may determine accuracy of its own clock. If the apparatus is the master device, it may receive the clock accuracy from one or more slave devices during the service discovery. The SCA parameter may be used in block 302 as well.

In some embodiments, the master and slave roles are not agreed to at this stage e.g., when the clock accuracy is provided by the server device in the advertisement message. For example, when the slave device has a more stable clock than the master device, the master device and the slave device may switch the master-slave roles so that the more accurate clock will serve as a master clock.

Then, the apparatus performs block 204 and determines if the combination of the clock accuracies results in synchronization accuracy that meets the requirements of the function or a Bluetooth service. The apparatus may use a function that maps the clock accuracies determined in blocks 300 and 302 to the synchronization accuracy. If the apparatus determines that the synchronization accuracy is acceptable, the apparatus may complete establishment of a Bluetooth service. Furthermore, the apparatus may carry out block 206 and carry out clock synchronization. Depending on the stage at which the apparatus acquires the clock accuracy of the other device, the completion of the establishment of the Bluetooth service may comprise different functions. For example, if the clock accuracy of the other device is received during the advertisement stage before transmission of a connection request, the apparatus determining that the synchronization accuracy is acceptable may transmit the connection request and establish the connection. If the clock accuracy of the other device is received after the connection setup in the detailed parameters of the service, the apparatus determining that the synchronization accuracy is acceptable may proceed with inquiring about the remaining parameters of the service. On the other hand, if the apparatus determines that the synchronization accuracy is not acceptable, the apparatus may terminate the connection setup, omit transmission of the connection request, or dismantle the established connection.

In an embodiment, the clock synchronization is maintained throughout the service. In another embodiment, the apparatus is configured to switch the clock synchronization on and off during the service. For example, in a case where the service is a measurement service, the apparatus may switch the synchronization on for the duration of carrying out measurements. In some cases, the measurements are carried out only periodically or at certain time instants while the service is maintained constantly. Accordingly, such switching of the synchronization may reduce the power consumption of the apparatus.

Figure 4:
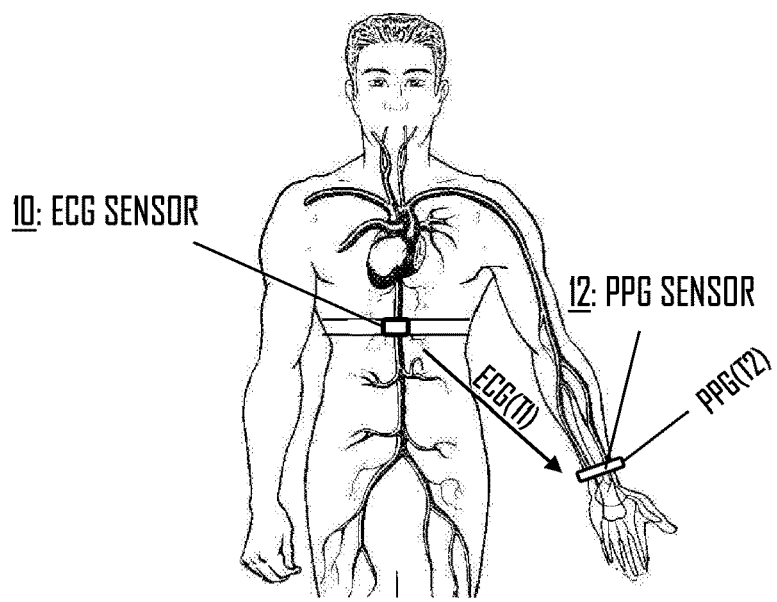
FIG. 4 illustrates an application employing synchronization according to an embodiment of the invention.
Figure 5:
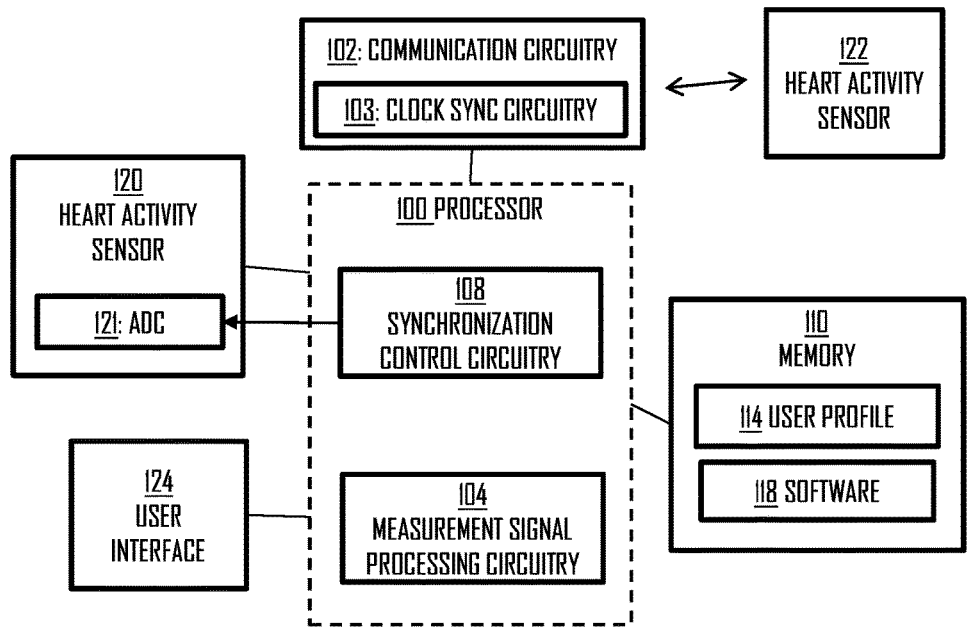
FIG. 5 illustrates a block diagram of an apparatus configured to synchronize measurement sampling timings according to an embodiment of the invention.

Let us now describe some applications where the synchronization is used. FIGS. 4 and 5 illustrate an embodiment where the clock synchronization is used in a measurement application. A measurement system may comprise a plurality of measurement devices coupled with the user's body. The measurement system may comprise any two or more of the sensor devices described above in connection with FIG. 1. FIG. 4 illustrates an embodiment where the system includes the ECG sensor 10 and the PPG sensor 12. The apparatus of FIG. 2 or 3 may be any one of the two sensor devices 10, 12, but let us assume now that the apparatus is the PPG sensor device 12. The measurement system may be configured to measure the PTT of the pulse wave velocity of a blood pulse travelling through the arteries of the user. Such a system may require high clock synchronization to enable accurate blood pressure measurements during a physical exercise, for example. The system may be used to evaluate other physiological characteristics on the basis of the PTT, such as the quality of sleep, stress levels, artery conditions, diseases, or disorders. Regarding the measurements, the ECG sensor 10 is capable of detecting when the blood pulse is generated in the heart. The ECG sensor may record a clock value at the detection timing T1 of the blood pulse and transmit T1 to the PPG sensor 12. Thereafter, the PPG sensor 12 detects the blood pulse from the wrist or another location of the human body where the PPG sensor is disposed. The PPG sensor then records the detection timing T2 of the blood pulse at the wrist. Now, with the knowledge of the distance between the heart and the wrist (or through appropriate preliminary calibration of a function), it is possible to compute the PTT or the pulse wave velocity. The accuracy of this computation is dependent on how well the clocks of the sensor devices 10 and 12 are synchronized with each other, i.e. how much additional deviation not related to the travel of the blood pulse is contained in the time difference T2-T1.

FIG. 5 illustrates a block diagram of an apparatus according to an embodiment of the invention. The apparatus may comprise an electronic device comprising at least one processor 100 and at least one memory 110. The processor 100 may form or be a part of a processing circuitry. The apparatus may further comprise a user interface 124 comprising a display screen or another display unit, an input device such as one or more buttons and/or a touch-sensitive surface, and an audio output device such as a loudspeaker. In some embodiments, the user interface 124 comprises a haptic output device configured to provide haptic indications to the user 20.

The processor 100 may comprise a measurement signal processing circuitry 104 configured to process measurement data acquired by using at least one sensor device of the apparatus or at least one sensor device external to the apparatus. The measurement signal processing circuitry 104 may comprise a time characteristics estimation circuitry configured to estimate time characteristics measurement signals acquired by using multiple sensor devices, such as the PTT from received measurement signals.

The apparatus may comprise a communication circuitry 102 connected to the processor 100. The communication circuitry may comprise hardware and software suitable for supporting Bluetooth® communication protocol such as Bluetooth Smart specifications. It should be appreciated that other communication protocols are equivalent solutions as long as they are suitable for establishing a personal area network (PAN) or suitable for measurement scenarios described in this document. The processor 100 may use the communication circuitry 102 to transmit and receive frames according to the supported wireless communication protocol. The frames may carry a payload data comprising the above-described measurement data such as ECG measurement data and/or PPG measurement data. In some embodiments, the processor 100 may use the communication circuitry 109 to transmit the measurement data, estimated time characteristics and/or the computed metrics to another apparatus, e.g. to a cloud server storing the user's 20 user account. The communication circuitry 102 may comprise a clock synchronization circuitry 103 configured to maintain clock synchronization with another apparatus when the clock synchronization circuitry 103 is activated.

In an embodiment, the apparatus comprises at least one heart activity sensor 120. The apparatus may comprise another sensor module to carry out other measurements. The heart activity sensor(s) 120 may comprise one or more of the above-described sensors such as an ECG sensor 10, PPG sensor 12, 14, and the BCG sensor 16. The heart activity sensor may comprise an analogue-to-digital converter (ADC) 121 configured to convert analogue measurement signals measured by a sensor head into digital signals. As known in the art, the ADC may contain a sampling circuitry configured to take discrete samples of an input analogue signal, and a quantization circuitry configured to quantize the samples to a determined accuracy determined by a word length of the ADC.

Additionally, the apparatus may communicate with at least one heart activity sensor 122 through the communication circuitry 102. The at least one heart activity sensor 122 may comprise an external heart activity sensor with respect to the apparatus. The heart activity sensor(s) 14 122 comprise different or different type(s) heart activity sensor(s) than the sensor(s) 12. In the embodiment where the apparatus comprises the other type of sensor module, the external heart activity sensor 122 may be replaced by another type of sensor device.

The processor may further comprise a synchronization control circuitry 108 configured to control the synchronization in the apparatus. The synchronization control apparatus may be configured to carry out blocks 200 to 204 of FIG. 2 and/or blocks 300 to 304 of FIG. 3. The synchronization control circuitry 108 may employ the communication circuitry 102 to acquire necessary information from other devices during the service discovery, for example. The synchronization control circuitry may be configured to control the operation of the clock synchronization circuitry 103 by switching it on and off.

In an embodiment, the synchronization control circuitry 108 is configured to control the ADC 121 while the clock synchronization circuitry is synchronizing the clock of the apparatus with a clock of another apparatus. The synchronization control circuitry 108 may control sampling timings of the sampling circuitry of the ADC 121 such that the sampling of the analogue measurement signals is carried out in synchronization with the other apparatus. Accordingly, any offset in the sampling instants between the sensor devices 10, 12, for example, may be avoided or reduced. This improves the accuracy of measurements sensitive to timing. Upon receiving an indication from the clock synchronization circuitry 108 that the clock synchronization has been achieved, the synchronization control circuitry 108 may configure the sampling timings of the ADC 121.

The memory may store a computer program product 118 defining the functions and processes executed by the processor 100. The memory 110 may further store one or more user profiles including a user profile of the user 20. The user profile may comprise attributes of the user 20 such as age, gender, height, weight, a maximum heart rate, and a fitness index. The memory may further store some operational parameters required for the operation of the apparatus, e.g. the required synchronization accuracies of one or more functions of the apparatus.

Figure 6:
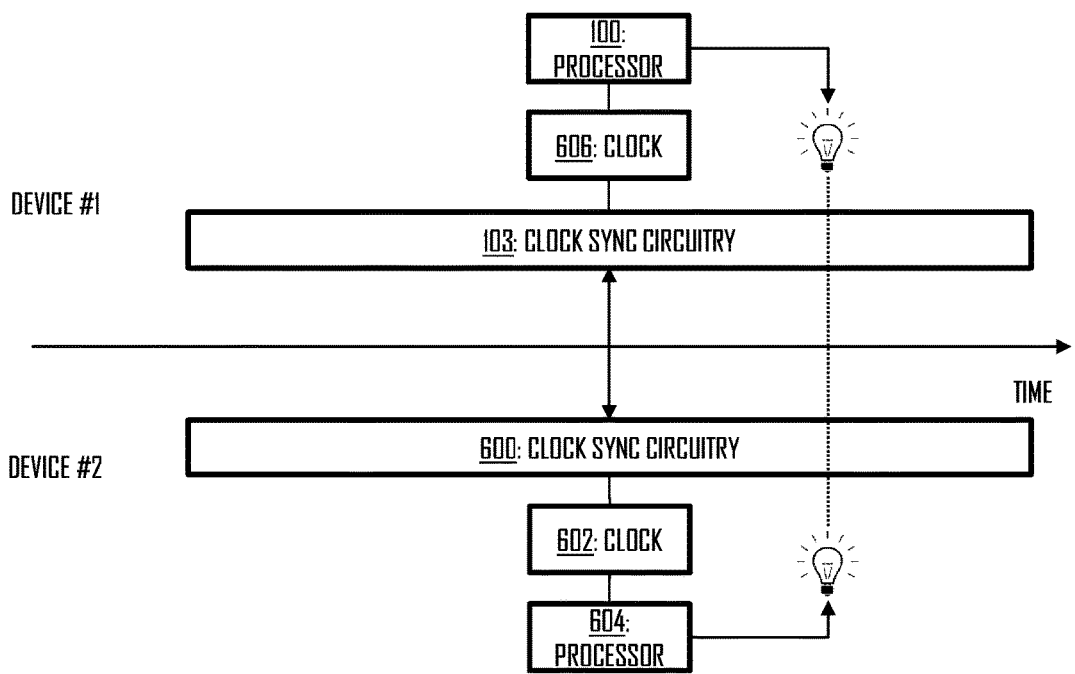
FIG. 6 illustrates another application employing synchronization according to an embodiment of the invention.

FIG. 6 illustrates another application that may benefit from the clock synchronization carried out in the above-described manner. In this embodiment, an output timing of an instruction signal output by the processor 100 is synchronized with the clock of the other apparatus. The apparatus of FIG. 5 may be configured to operate as described in connection with FIG. 6, or another apparatus may be configured to operate as described in connection with FIG. 6. For example, the sensor devices 120, 122 and the measurement signal processing 104 are not mandatory for the embodiment of FIG. 6. Referring to FIG. 6, clock synchronization circuitries 103, 600 of the apparatuses maintain synchronization on a regular basis. The synchronization may be maintained as described below in connection with FIG. 7, for example. As a result, the clocks 602, 606 of the apparatuses are synchronized with each other. An application executed by the processors 100, 604 of the apparatuses may comprise an instruction to output a determined control signal or instructions signal at a determined timing defined by a clock value output by the respective clocks 602, 606. In this simple example, the output control signal illuminates a lamp represented by bulbs in FIG. 6. When the clocks 602, 606 are synchronized accurately, the lamps are lit at the same time, as indicated in FIG. 6 the dotted line crossing a time axis.

In other embodiments, the lamp may be replaced by another device. The device may be a user interface indicator such as an illuminating device or an audio output device. The device may, however, be another type of device, e.g. a camera having imaging triggered by the control signal, a flashlight for the camera, control components of an industrial process such as valves, loudspeakers of a multi-channel loudspeaker system (in which case the control signal may be replaced by a data signal representing audio data being played). In general, the accurate clock synchronization may be utilized to execute the same function in the different apparatuses exactly at the same time. The required synchronization accuracy may be specified for an application comprising the function in order to facilitate the execution of embodiment of FIG. 2 or 3.

Figure 7:
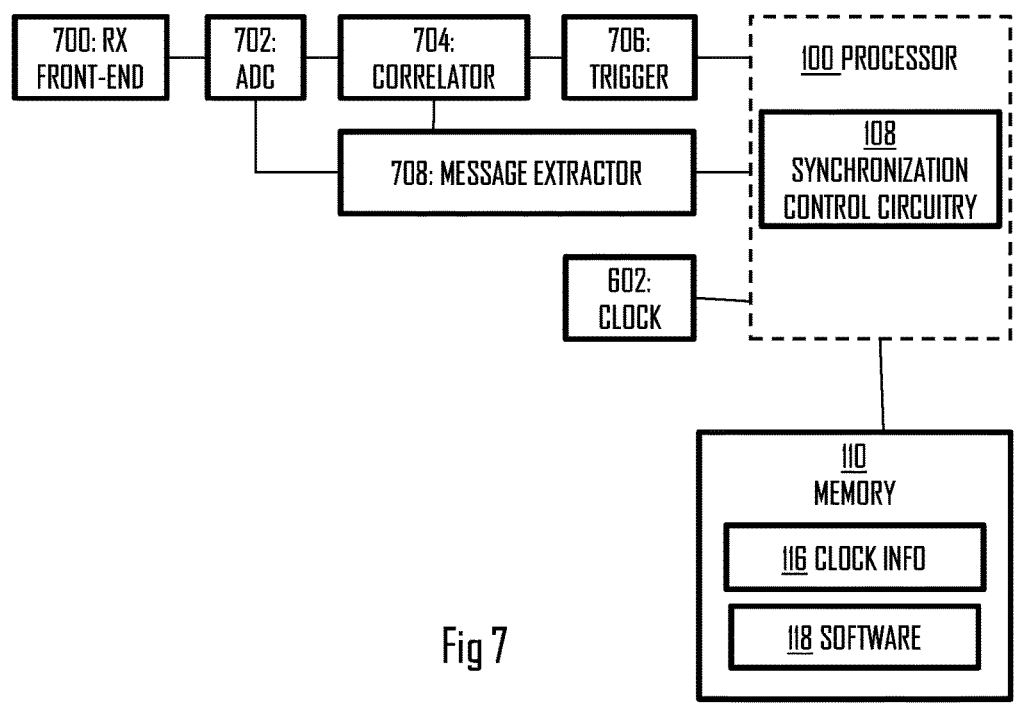
FIG. 7 illustrates a block diagram of a synchronization circuitry according to an embodiment of the invention.

Let us now describe an embodiment for maintaining the synchronization with reference to FIG. 7. FIG. 7 illustrates an embodiment of the apparatus of FIG. 5 although the structure of FIG. 7 may be implemented in another apparatus as well. Referring to FIG. 7, the apparatus may be configured to receive a frame through the communication circuitry 102 comprising radio frequency front-end components 700, a frequency-converter configured to convert the radio frequency frame into a baseband, and an ADC 702 configured to digitize the radio frame. The digitized frame may be input to a correlator 704 and a message extractor 708. The correlator 704 may be configured to search for a determined sequence from the received frame. The determined sequence may be a sequence associated with the other apparatus with which the apparatus has established the service associated with the application requiring the clock synchronization. The determined sequence may be a sequence the other apparatus inserts into every frame it transmits. The determined sequence may be a sequence the other apparatus inserts into most frames it transmits. The determined sequence may be a sequence the other apparatus inserts into every frame it transmits periodically. In an embodiment, the determined sequence is an access address or a device address of the other apparatus.

The correlator 704 may be configured with the determined sequence such that, upon the determined sequence enters the correlator completely, the correlator outputs a signal to a trigger circuitry 706. The trigger circuitry may configure the processor 100 to mark a current value of the clock 602 as reception timing of the frame. The determined sequence may be used as an anchor point for the clock synchronization in the apparatus. The correlator 704 or the trigger circuitry 706 may also trigger a message extractor circuitry 708 to start extracting contents of the received frame at this instant when it has been verified that the received frame is associated with the other apparatus. The correlator 704 and the trigger circuitry 706 may be parts of the clock synchronization circuitry 103 while the ADC 702, the receiver front-end 700, and the message extractor circuitry 708 may be parts of the communication circuitry 102.

In an embodiment, the apparatuses regularly transmit a frame comprising a current clock value of the transmitting apparatus. The clock value may indicate the clock value at the transmission timing of the frame. Some processing delays of the transmitting apparatus may be incorporated into the clock value such that the clock value accurately represents the clock value of the transmitting apparatus at an instant when the frame exits from analogue transmission circuitries of the transmitting apparatus. A frame transmitted by the transmitting apparatus and received by the apparatus may have the following format:

TABLE 1

| Bluetooth version | Preamble | Access Address | PDU including clock value | CRC |
|---|---|---|---|---|
| Bluetooth v4.0 and v4.1 | 1 octet | 4 octets | 2 to 39 octets | 3 octets |
| Bluetooth v4.2 or later | 1 octet | 4 octets | 2 to 257 octets | 3 octets |

PDU represents a protocol data unit. The message extractor circuitry 708 may be configured to extract the clock value indicating the transmission timing of the frame from the received frame and output the clock value to the synchronization control circuitry 108.

The synchronization control circuitry 108 may be configured to synchronize the clock 602 the clock of the other apparatus at least partly on the basis of the clock value extracted from the received frame and the reception timing of the frame indicated by the value of the clock 602 marked as a result of the triggering by the trigger circuitry 706. The memory 110 may store clock information 116 comprising any offset to be applied to the clock value during the synchronization. The clock information may indicate processing delay in the apparatus from the front-end 700 to the output of the correlator circuitry 704. In an embodiment, the apparatus is configured to monitor for the distance between the apparatus and the other apparatus, to estimate a radio propagation delay associated with the distance, and to store the radio propagation delay as the clock information. The radio propagation delay may be estimated by using any one of state-of-the-art delay estimation algorithms, e.g. by using received signal strength (RSS) estimation or positioning of the apparatuses. In another embodiment, e.g. in PAN solutions, the radio propagation delay may be negligible. By taking various delays into account, the clock synchronization accuracy may be improved.

As used in this application, the term 'circuitry' refers to all of the following: (a) hardware-only circuit implementations, such as implementations in only analog and/or digital circuitry, and (b) combinations of circuits and software (and/or firmware), such as (as applicable): (i) a combination of processor(s) or (ii) portions of processor(s)/software including digital signal processor(s), software, and memory(ies) that work together to cause an apparatus to perform various functions, and (c) circuits, such as a microprocessor(s) or a portion of a microprocessor(s), that require software or firmware for operation, even if the software or firmware is not physically present. This definition of 'circuitry' applies to all uses of this term in this application. As a further example, as used in this application, the term 'circuitry' would also cover an implementation of merely a processor (or multiple processors) or a portion of a processor and its (or their) accompanying software and/or firmware. The term 'circuitry' would also cover, for example and if applicable to the particular element, a baseband integrated circuit or applications processor integrated circuit for a mobile phone or a similar integrated circuit in a server, a cellular network device, or another network device.

In an embodiment, at least some of the processes described in connection with FIGS. 2 to 7 may be carried out by an apparatus comprising corresponding means for carrying out at least some of the described processes. Some example means for carrying out the processes may include at least one of the following: detector, processor (including dual-core and multiple-core processors), digital signal processor, controller, receiver, transmitter, encoder, decoder, memory, RAM, ROM, software, firmware, display, user interface, display circuitry, user interface circuitry, user interface software, display software, circuit, and circuitry. In an embodiment, the at least one processor 100, the memory 110, and the computer program code 118 form processing means or comprises one or more computer program code portions for carrying out one or more operations according to any one of the embodiments of FIGS. 2 to 7 or operations thereof.

The techniques and methods described herein may be implemented by various means. For example, these techniques may be implemented in hardware (one or more devices), firmware (one or more devices), software (one or more modules), or combinations thereof. For a hardware implementation, the apparatus(es) of embodiments may be implemented within one or more application-specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described herein, or a combination thereof. For firmware or software, the implementation can be carried out through modules of at least one chipset (e.g. procedures, functions, and so on) that perform the functions described herein. The software codes may be stored in a memory unit and executed by processors. The memory unit may be implemented within the processor or externally to the processor. In the latter case, it can be communicatively coupled to the processor via various means, as is known in the art. Additionally, the components of the systems described herein may be rearranged and/or complemented by additional components in order to facilitate the achievements of the various aspects, etc., described with regard thereto, and they are not limited to the precise configurations set forth in the given figures, as will be appreciated by one skilled in the art.

Embodiments as described may also be carried out in the form of a computer process defined by a computer program or portions thereof. Embodiments of the methods described in connection with FIGS. 2 to 7 may be carried out by executing at least one portion of a computer program comprising corresponding instructions. The computer program may be in source code form, object code form, or in some intermediate form, and it may be stored in some sort of carrier, which may be any entity or device capable of carrying the program. For example, the computer program may be stored on a computer program distribution medium readable by a computer or a processor. The computer program medium may be, for example but not limited to, a record medium, computer memory, read-only memory, electrical carrier signal, telecommunications signal, and software distribution package, for example. The computer program medium may be a non-transitory medium. Coding of software for carrying out the embodiments as shown and described is well within the scope of a person of ordinary skill in the art.

It will be obvious to a person skilled in the art that, as the technology advances, the inventive concept can be implemented in various ways. The invention and its embodiments are not limited to the examples described above but may vary within the scope of the claims.

The invention claimed is:

1. A method comprising:
storing, in a first sensor apparatus, information representing synchronization accuracy required by a heart pulse transit time measurement function of the first sensor apparatus;

carrying out, by the first sensor apparatus with a second sensor apparatus, a service discovery procedure of a service providing the heart pulse transit time measurement function, and receiving a universally unique identifier of the service and clock information from the second sensor apparatus during the service discovery procedure, wherein each of the first sensor apparatus and the second sensor apparatus comprises a wearable sensor apparatus;

determining, by the first sensor apparatus on the basis of the received clock information and said stored information, whether or not synchronization accuracy is sufficient for the heart pulse transit time measurement function;

upon determining that the synchronization accuracy is sufficient for the heart pulse transit time measurement function, synchronizing a clock of the first sensor apparatus with a clock of the second sensor apparatus; and processing measurement data acquired using the first sensor apparatus and the second sensor apparatus to compute a pulse transit time of a heart pulse wave, the measurement data comprising a first detection time indicating when the first sensor apparatus detected the heart pulse wave and a second detection time indicating when the second sensor apparatus detected the heart pulse wave.

2. The method of claim 1, wherein the received clock information comprises a clock accuracy of the second sensor apparatus.

3. The method of claim 1, wherein said determining is further based on clock information of the first sensor apparatus.

4. The method of claim 1, wherein said synchronizing the clock of the first sensor apparatus comprises synchronizing a clock of an analogue-to-digital converter of a measurement circuitry of the first sensor apparatus with the clock of the second sensor apparatus.

5. The method of claim 4, wherein said synchronizing the clock of the analogue-to-digital converter of the measurement circuitry of the first sensor apparatus comprises synchronizing sampling timing of the analogue-to-digital converter with the clock of the second sensor apparatus.

6. The method of claim 1, wherein said synchronizing the clock of the first sensor apparatus comprises synchronizing an output timing of an instruction signal output by a processor of the first sensor apparatus with the clock of the second sensor apparatus.

7. The method of claim 1, wherein the first sensor apparatus and the second sensor apparatus operate according to a short range wireless communication protocol.

8. The method of claim 1, wherein said synchronizing the clock of the first sensor apparatus with the clock of the second sensor apparatus comprises:
receiving a frame;
searching for a determined sequence from the received frame;
upon detecting the determined sequence in the frame, marking a current value of the clock of the first sensor apparatus as reception timing of the frame;
associating the received frame with the second apparatus;
extracting, from the received frame, a clock value indicating transmission timing of the frame; and
synchronizing the clock of the first sensor apparatus with the clock of the second sensor apparatus at least partly on the basis of the clock value extracted from the received frame and the reception timing of the frame indicated by the marked value of the clock of the first sensor apparatus.

9. The method of claim 8, wherein the determined sequence is an access address of the second sensor apparatus.

10. The method of claim 8, wherein said synchronizing the clock of the first sensor apparatus with the clock of the second sensor apparatus is further based on a value representing channel delay between the first sensor apparatus and the second sensor apparatus and processing delay in the first sensor apparatus before said marking.

11. A sensor apparatus comprising:
a memory device,
a clock, and
a processing circuitry configured to perform operations comprising:
storing, in the memory, information representing synchronization accuracy required by a heart pulse transit time measurement function of the sensor apparatus;
carrying out, with another sensor apparatus, a service discovery procedure of a service providing the heart pulse transit time measurement function and receiving a universally unique identifier of the service and clock information from the other sensor apparatus during the service discovery procedure, wherein each of the sensor apparatus and the other sensor apparatus comprises a wearable sensor apparatus;
determining, on the basis of the received clock information and said stored information, whether or not synchronization accuracy is sufficient for the heart pulse transit time measurement function;
upon determining that the synchronization accuracy is sufficient for the heart pulse transit time measurement function, synchronizing the clock with a clock of the other sensor apparatus; and
processing measurement data acquired using the sensor apparatus and the other sensor apparatus to compute pulse transit time of a heart pulse wave, the measurement data comprising a first detection time indicating when the first sensor apparatus detected the heart pulse wave and a second detection time indicating when the second sensor apparatus detected the heart pulse wave.

12. The sensor apparatus of claim 11, wherein the received clock information comprises a clock accuracy of the other sensor apparatus.

13. The sensor apparatus of claim 11, wherein the processing circuitry is configured to carry out said determining further based on clock information of the clock of the sensor apparatus.

14. The sensor apparatus of claim 11, wherein the operations further comprise synchronizing a clock of an analogue-to-digital converter of a measurement circuitry of the sensor apparatus with the clock of the other sensor apparatus.

15. The sensor apparatus of claim 14, wherein the operations further comprise synchronizing sampling timing of the analogue-to-digital converter with the clock of the other sensor apparatus.

16. The sensor apparatus of claim 11, wherein the operations further comprise synchronizing an output timing of an instruction signal output by the processing circuitry with the clock of the other sensor apparatus.

17. The sensor apparatus of claim 11, further comprising a communication circuitry configured to operate according to short range wireless communication protocol.

18. The sensor apparatus of claim 11, wherein the operations further comprise at least the following in connection with synchronizing the clock with the clock of the other sensor apparatus:
receiving a frame;
searching for a determined sequence from the received frame;
upon detecting the determined sequence in the frame, marking a current value of the clock as reception timing of the frame;
associating the received frame with the other sensor apparatus;
extracting, from the received frame, a clock value indicating transmission timing of the frame; and
synchronizing the clock with the clock of the other sensor apparatus at least partly on the basis of the clock value extracted from the received frame and the reception timing of the frame indicated by the marked value of the clock.

19. The sensor apparatus of claim 18, wherein the determined sequence is an access address of the other sensor apparatus.

20. The sensor apparatus of claim 18, wherein the operations further comprise performing said synchronizing the clock with the clock of the other sensor apparatus further as based on a value representing channel delay between the sensor apparatus and the other sensor apparatus and a value representing processing delay before said marking in the apparatus.

21. A computer program product embodied on a non-transitory computer-readable medium readable by a computer and configured to cause the computer to execute a computer process comprising:
storing, in a first sensor apparatus, information representing synchronization accuracy required by a heart pulse transit time measurement function of the first sensor apparatus;
carrying out, by the first sensor apparatus with a second sensor apparatus, a service discovery procedure of a service providing the heart pulse transit time measurement function, and receiving a universally unique identifier of the service and clock information from the second sensor apparatus during the service discovery procedure, wherein each of the first sensor apparatus and the second sensor apparatus comprises a wearable sensor apparatus;
determining, by the first sensor apparatus on the basis of the received clock information and said stored information, whether or not synchronization accuracy is sufficient for the heart pulse transit time measurement function;
upon determining that the synchronization accuracy is sufficient for the heart pulse transit time measurement function, synchronizing a clock of the first sensor apparatus with a clock of the second sensor apparatus; and
processing measurement data acquired using the first sensor apparatus and the second sensor apparatus to compute pulse transit time of a heart pulse wave, the measurement data comprising a first detection time indicating when the first sensor apparatus detected the heart pulse wave and a second detection time indicating when the second sensor apparatus detected the heart pulse wave.

22. The method of claim 1, wherein upon determining that the synchronization accuracy is not sufficient for the heart activity measurement function, terminating a connection setup with the second sensor apparatus, omitting transmission of a connection request to the second sensor apparatus, or dismantling an established connection with the second sensor apparatus.

23. The sensor apparatus of claim 11, wherein the operations further comprise, upon determining that the synchronization accuracy is not sufficient for the at least one heart activity measurement function, to terminate a connection setup with the second sensor apparatus, omit transmission of a connection request to the second sensor apparatus, or dismantle an established connection with the second sensor apparatus.

* * * * *